(12) United States Patent
Kato et al.

(10) Patent No.: US 8,525,029 B2
(45) Date of Patent: Sep. 3, 2013

(54) VEHICLE ELECTRICAL CONDUCTION PATH

(75) Inventors: Koichi Kato, Hitachi (JP); Hajime Maejo, Hitachi (JP); Toshiyuki Horikoshi, Mito (JP)

(73) Assignee: Hitachi Cable, Ltd., Tokyo (JP)

( * ) Notice: Subject to any disclaimer, the term of this patent is extended or adjusted under 35 U.S.C. 154(b) by 140 days.

(21) Appl. No.: 12/926,994

(22) Filed: Dec. 22, 2010

(65) Prior Publication Data

US 2011/0155458 A1 Jun. 30, 2011

(30) Foreign Application Priority Data

Dec. 24, 2009 (JP) ................................. 2009-293096
Mar. 31, 2010 (JP) ................................. 2010-081884

(51) Int. Cl.
*H01B 11/02* (2006.01)

(52) U.S. Cl.
USPC ...................................................... 174/113 R

(58) Field of Classification Search
USPC ................... 174/113 R, 71 R, 72 R, 112
See application file for complete search history.

(56) References Cited

U.S. PATENT DOCUMENTS

| | | | | |
|---|---|---|---|---|
| 4,491,713 A * | 1/1985 | Patton et al. | ............... | 219/69.11 |
| 6,249,913 B1 * | 6/2001 | Galipeau et al. | ................ | 725/76 |
| 7,094,970 B2 | 8/2006 | Kihira | | |
| 7,592,549 B2 * | 9/2009 | Seufert et al. | ............. | 174/113 R |
| 7,687,714 B2 * | 3/2010 | Deterre et al. | ............... | 174/72 R |
| 7,918,685 B1 * | 4/2011 | Kruckenberg | ................ | 439/502 |
| 2003/0121694 A1 * | 7/2003 | Grogl et al. | ............... | 174/113 R |
| 2004/0099427 A1 | 5/2004 | Kihira | | |
| 2005/0090151 A1 * | 4/2005 | Laity et al. | .................... | 439/607 |
| 2006/0278423 A1 | 12/2006 | Ichikawa et al. | | |
| 2008/0041622 A1 | 2/2008 | Seufert et al. | | |

FOREIGN PATENT DOCUMENTS

| | | |
|---|---|---|
| DE | 10 2005 054 926 A1 | 6/2006 |
| EP | 1 873 791 A2 | 1/2008 |
| JP | 2003-92028 A | 3/2003 |
| JP | 2003-219530 A | 7/2003 |
| JP | 2004-171952 A | 6/2004 |
| JP | 2006-310125 A | 11/2006 |
| JP | 2007-087628 A | 4/2007 |
| JP | 2007-87628 A | 4/2007 |
| JP | 2009-123635 A | 6/2009 |

OTHER PUBLICATIONS

Extended European Search Report dated May 7, 2013.

* cited by examiner

*Primary Examiner* — Chau Nguyen
(74) *Attorney, Agent, or Firm* — McGinn IP Law Group, PLLC

(57) ABSTRACT

A vehicle electrical conduction path includes plural power cables, a braided shield which bundles and shields the plural power cables, a control cable, a metallic pipe which accommodates the control cable separately from the plural power cables, and a flexible resin tube which covers a periphery of the metallic pipe and the plural power cables bundled with the braided shield and arranged along the metallic pipe.

20 Claims, 7 Drawing Sheets

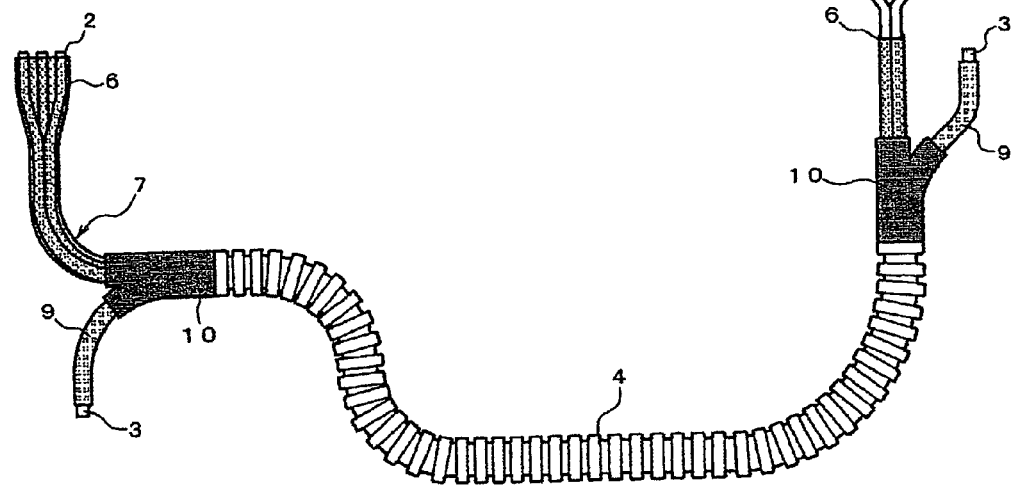
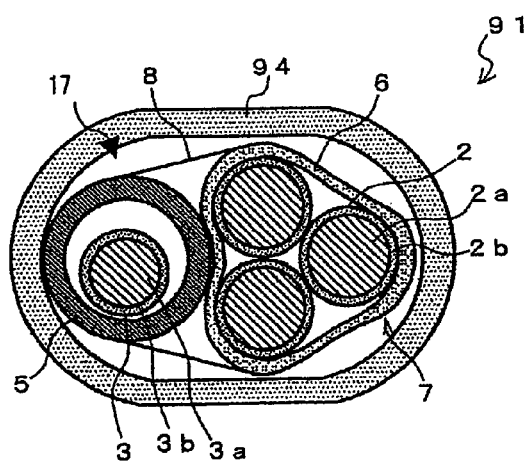

VEHICLE ELECTRICAL CONDUCTION PATH

The present application is based on Japanese patent application No. 2009-293096 filed on Dec. 24, 2009 and Japanese patent application No. 2010-081884 filed on Mar. 31, 2010, the entire contents of which are incorporated herein by reference.

BACKGROUND OF THE INVENTION

1. Field of the Invention

The present invention relates to a vehicle electrical conduction path for use in hybrid vehicles, electric vehicles and the like.

2. Description of the Related Art

Conventional vehicle electrical conduction paths for use in hybrid vehicles, electric vehicles and the like have been disclosed in JP-A-2004-171952 and JP-A-2007-87628.

JP-A-2004-171952 discloses a vehicle electrical conduction path having a plurality of electric cables collectively accommodated in a metallic pipe. The vehicle electrical conduction path is required to be held in a desired wiring shape (layout), for example at a lower surface of a vehicle body, as well as having a shield means, in view of an effect of noise on a device mounted on a vehicle or a control cable (herein referred to as the device mounted on the vehicle). JP-A-2004-171952 allows the noise on the device mounted on the vehicle to be inhibited by accommodating the plurality of the electric cables in the metallic pipe serving as the shield means, and the plurality of the electric cables to be held in the desired wiring shape by forming the metallic pipe into the desired wiring shape.

Also, JP-A-2007-87628 discloses a vehicle electrical conduction path having a control cable and an auxiliary power cable accommodated in an inner metallic pipe, and the inner metallic pipe with the control cable and the auxiliary power cable accommodated therein, and a main power cable accommodated in an outer metallic pipe. JP-A-2007-87628 can, as with JP-A-2004-171952, hold a desired wiring shape (layout), and allows noise caused in the main power cable in which large current flows, to be inhibited from affecting electrical signals propagating in the control cable, because the inner metallic pipe serves as a shield for the control cable. Also, the outer metallic pipe can serve as a shield to inhibit the effect of noise caused in the main power cable in which large current flows, on the device mounted on the vehicle.

The vehicle electrical conduction paths are for connecting e.g. between a motor and an inverter, or between an inverter and a battery, in hybrid vehicles, electric vehicles and the like. For that, high voltage current flows in power cables of the vehicle electrical conduction paths connecting therebetween. These electrical conduction paths in which high voltage current flows are colored in a predetermined color (orange color for indicating high voltage portion) standardized in compliance with an international standard.

In JP-A-2004-171952 and JP-A-2007-87628, since the member positioned at the outermost layer is the metallic pipe, this metallic pipe is painted in the predetermined color. However, there arises the problem that this painting is very time-consuming and costly due to requiring heat resistance, and mechanical strength (adherence) causing no peeling during forming process, and also due to needing a good even coating in view of reliability thereof.

To save such labor in the painting, the inventors have contemplated accommodating the power cable and the control cable in a corrugated tube made of a resin colored beforehand. The corrugated tube is an accordion hollow tube, also called slit tube, flexible electrical conduit, etc.

When the power cable or the control cable is accommodated in the corrugated tube, there arises the problem, however, that the power cable and the control cable cannot be held in a desired wiring shape due to the flexibility of the corrugated tube.

The technique contemplated to overcome this problem and allow the power cable and the control cable to be held in a desired wiring shape is, for example, to accommodate the control cable with enhanced rigidity in the corrugated tube, form the control cable in the desired wiring shape, and lay the power cable along the control cable, thereby holding the vehicle electrical conduction path in the desired wiring shape.

Refer to JP-A-2004-171952, JP-A-2007-87628, and JP-A-2009-123635, for example.

A rigid structure of a vehicle electrical conduction path portion to be connected to a device mounted on a vehicle (herein referred to as the device) is not preferred because a cable break thereof is caused by stress due to vehicle vibration acting on the portion connecting the vehicle electrical conduction path and the device. For that, the vehicle electrical conduction path portion to be connected to the device needs to be structured to be flexible.

When the control cable with enhanced rigidity is accommodated in the corrugated tube as described above, there is therefore the problem that its portion to be connected to the device has to be very inconveniently reconnected to a flexible cable, and connected via the flexible cable to the device.

SUMMARY OF THE INVENTION

Accordingly, it is an object of the present invention to provide a vehicle electrical conduction path, which overcomes the above problems, and which allows the ease of production, and the ease of connection to a device.

According to a feature of the invention, a vehicle electrical conduction path comprises:

plural power cables;

a braided shield which bundles and shields the plural power cables;

a control cable;

a metallic pipe which accommodates the control cable separately from the plural power cables; and a flexible resin tube which covers a periphery of the metallic pipe and the plural power cables bundled with the braided shield and arranged along the metallic pipe.

The metallic pipe may be configured to hold the control cable in a desired shape.

The metallic pipe preferably accommodates only the control cable.

The metallic pipe may be formable in a desired shape for accommodating the control cable.

A rigidity of the metallic pipe is preferably greater than a rigidity of the flexible resin tube.

The control cable may be accommodated in the metallic pipe and the metallic pipe accommodating the control cable may be formed in a desired shape, thereby holding the control cable in the desired shape.

It is preferable that an end of the metallic pipe is electrically connected with one end of a flexible shielded wire, a periphery of the control cable extended out from the end of the metallic pipe is covered with the shielded wire, and another end of the shielded wire extended out from an end of the resin tube is configured to be electrically connected with a shield case for a device to which the control cable is connected.

The braided shield extended out from an end of the resin tube may be configured to be electrically connected with a shield case for a device to which the plural power cables are connected.

The vehicle electrical conduction path may further comprise:

a protective member for protecting a branching portion at an end of the resin tube, from which the plural power cables bundled with the braided shield and the control cable branch.

Portions of the control cable and the plural power cables bundled with the braided shield may be extended from the branching portion and fitted into flexible resin terminal tubes, respectively.

The resin tube may comprise a corrugated tube.

The metallic pipe may be formed into a desired shape, prior to the plural power cables bundled with the braided shield being arranged along the metallic pipe.

The metallic pipe and the plural power cables bundled with the braided shield may be made integral with each other by being bound with a taping material.

The plural power cables bundled with the braided shield may be arranged in a substantially C-shape in its cross-sectional view along a periphery of the metallic pipe, and a periphery of the plural power cables with the braided shield and the metallic pipe may be covered with the resin tube having a circular cross section.

The plural power cables bundled with the braided shield may be arranged along one side of the metallic pipe, and a periphery of the plural power cables with the braided shield and the metallic pipe may be covered with the resin tube having an elliptic cross section.

The vehicle electrical conduction path may further comprise:

an insulating layer provided between the metallic pipe and the braided shield.

The insulating layer may cover at least one of a periphery of the metallic pipe and a periphery of the braided shield.

The insulating layer may be formed in a mesh-like shape.

(Points of the Invention)

According to the embodiments of the invention, since only the plural power cables are bundled with the braided shield, and the plural power cables bundled with the braided shield are arranged along the metallic pipe with the control cable accommodated therein, the power cables and the control cable are easily allowed to branch. Further, the branching portions of the power cables of the vehicle electrical conduction path are covered with the braided shield and therefore do not have to be provided with a separate shield. This allows the ease of connection of the power cables to devices. Also, in the vehicle electrical conduction path, the control cable extended out from the metallic pipe is allowed to be connected directly to the devices. This allows the ease of connection of the control cable to the devices.

BRIEF DESCRIPTION OF THE DRAWINGS

The preferred embodiments according to the invention will be explained below referring to the drawings, wherein:

FIG. 8 is a plan view showing providing a protective member to branching portions in the method for producing the vehicle electrical conduction path shown in FIGS. 1A and 1B;

FIG. 9 is a cross-sectional view showing a vehicle electrical conduction path in a second embodiment according to the invention;

DETAILED DESCRIPTION OF THE PREFERRED EMBODIMENTS

Below are described preferred embodiments according to the invention, referring to the accompanying drawings.

First Embodiment

Figure 1A:
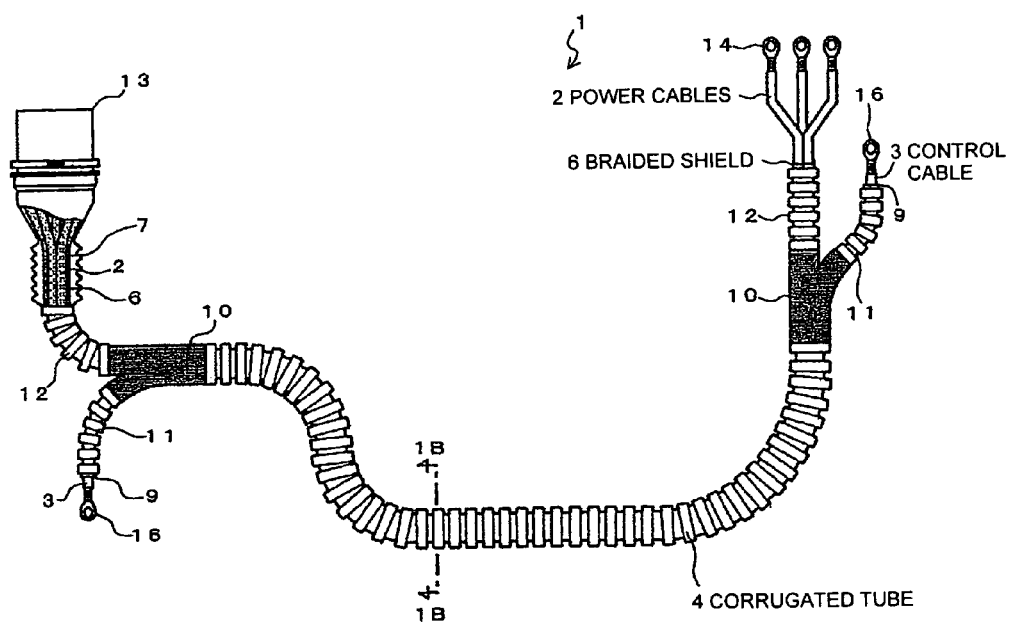
FIG. 1A is a plan view showing a vehicle electrical conduction path in a first embodiment according to the invention.
Figure 1B:
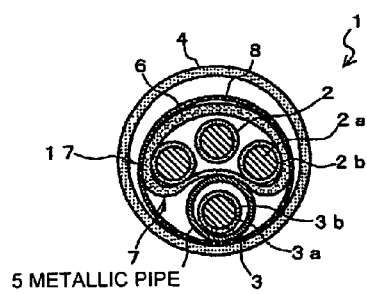
FIG. 1B is a cross-sectional view taken along line 1B-1B in FIG. 1A.

FIG. 1A is a plan view showing a vehicle electrical conduction path in a first preferred embodiment according to the invention, and FIG. 1B is a cross-sectional view taken along line 1B-1B in FIG. 1A.

(Structure of a Vehicle Electrical Conduction Path 1)

A vehicle electrical conduction path 1 in the first preferred embodiment according to the invention comprises a plurality of power cables 2, a braided shield 6 for bundling and shielding the plural power cables 2, at least one control cable 3, a metallic pipe 5 for being formable or moldable into a desired shape into which the control cable 3 is accommodated; and a corrugated tube 4 for serving as a flexible resin tube, wherein the plural power cables 2 bundled with the braided shield 6 are arranged along the metallic pipe 5, and a periphery thereof is covered with the corrugated tube 4.

In other words, the vehicle electrical conduction path 1 comprises the power cables 2, the braided shield 6 which bundles and shields the plural power cables 2, the control cable 3, the metallic pipe 5 which accommodates the control cable 3 separately from the plural power cables 2, and the corrugated tube (flexible resin tube) 4 which covers a periphery of the metallic pipe 5 and the plural power cables 2 bundled with the braided shield 6 and arranged along the metallic pipe 5. The metallic pipe 5 is configured to hold the control cable in a desired shape at, and comprises a metal material which is formable or moldable in the desired shape for accommodating the control cable 3. The metallic pipe 5 accommodates only the control cable and does not accommodates the plural power cables 2.

As shown in FIGS. 1A and 1B, the vehicle electrical conduction path 1 is constructed by accommodating the plural power cables 2 bundled with the braided shield 6, and at least one control cable 3 into the corrugated tube 4.

(Cables)

In this embodiment, there is described the case of use of four cables in total: three power cables 2 assumed as being for three phase alternating current, and one control cable 3. The power cables 2 used are each coated with an insulation 2b around a central conductor 2a, and are 7.0 mm in outside diameter thereof in this embodiment. The control cable 3 used is coated with an insulation 3b around a central conductor 3a, and is 7.0 mm in outside diameter thereof in this embodiment. The control cable 3 is used for a CAN (Controller Area Network), for example.

(Corrugated Tube 4)

The corrugated tube 4 is colored beforehand in a predetermined color (orange color for indicating high voltage portion). The resin used for the corrugated tube 4 is not particularly limited, but preferably uses a resin with good heat resistant property and fire retardant property. Also, the resin used for the corrugated tube 4 preferably has such a strength as to allow the plural power cables 2 bundled with the braided shield 6 and the metallic pipe 5 to be protected from an external interfering object (e.g. a flying stone). In this embodiment, the corrugated tube 4 is used as the flexible resin tube. The corrugated tube 4 is also desirably used for the vehicle electrical conduction path 1 from the point of view of its advantageously good heat dissipation. In this embodiment, the corrugated tube 4 used is 25.0 mm in inside diameter and 30.0 mm in maximum outside diameter. The resin tube is not limited to the corrugated tube, but may use any flexible resin or rubber tube.

In the vehicle electrical conduction path 1, the control cable 3 is accommodated in the metallic pipe 5, and the metallic pipe 5 with the control cable 3 accommodated therein is formed into a desired shape, thereby holding the control cable 3 in the desired shape, and the plural power cables 2 are collectively bundled with the braided shield 6, and the plural power cables 2 collectively bundled and shielded with the braided shield 6 are arranged along the formed metallic pipe 5, and a periphery thereof is covered with the corrugated tube 4.

(Metallic Pipe 5)

The metallic pipe 5 has a mechanical strength which is sufficient for holding the control cable 3 in the desired shape at a normal state. The rigidity of the metallic pipe 5 is greater than a rigidity of the corrugated tube 4 such that the desired shape of the vehicle conduction path 1 is maintained while using the corrugated tube 4 made of a flexible resin. A length of the metallic pipe 5 is preferably longer than a length of the corrugated tube 4 so as to sufficiently protect the control cable 3. The metallic pipe 5 may be a seamless pipe formed by drawing or extruding a metal sheet. Alternatively, the metallic pipe 5 may be divided into plural sections, e.g. two portions, so as to facilitate the installation of the control cable 3 in the metallic pipe 5.

The metallic pipe 5 may use e.g. aluminum which is light weight and low cost. To hold strength of the metallic pipe 5, it is desirable that the metallic pipe 5 has a thickness of 1 mm or more. This is because the metallic pipe 5 having a thickness less than 1 mm is not likely to hold its strength, but cause the vehicle electrical conduction path 1 itself to sag under its own weight. This metallic pipe 5 serves both to hold the desired wiring shape, and to shield the control cable 3. In this embodiment, the metallic pipe 5 used is 9.0 mm in inside diameter, 12.0 mm in outside diameter, and 1.5 mm in thickness.

(Braided Shield 6)

The braided shield 6 is formed of a braided metal wire such as a braided copper or aluminum wire. From the point of view of weight reduction, it is desirable to use a braided aluminum metal wire as the braided shield 6. The braided shield 6 serves as a shield to allow noise (electromagnetic waves) caused in the power cables 2 to radiate out and thereby be inhibited from affecting the device mounted on the vehicle. In this embodiment, the braided shield 6 is 1.0 mm thick. Herein, the plural power cables 2 bundled with the braided shield 6 are referred to as power cable bundle 7.

(Power Cable Bundle 7)

The power cable bundle 7 is arranged along the formed metallic pipe 5, and the metallic pipe 5 and the power cable bundle 7 are bound and fixed together at positions longitudinally spaced a predetermined pitch apart using a taping material 8. The taping material 8 may use any of an adhesive tape, a non-adhesive tape, or a plastic band. In this embodiment, the taping material 8 used is 0.5 mm in thickness. The power cable bundle 7 along the metallic pipe 5 is arranged in a substantially C-shape in its cross-sectional view along a periphery of the metallic pipe 5 (see FIG. 1B).

The corrugated tube 4 is formed to have such a length as to cover the entire metallic pipe 5 (that is a length slightly shorter than the metallic pipe 5). At ends of the corrugated tube 4, the control cable 3 and the power cable bundle 7 extended out from the corrugated tube 4 branch. These branching portions are provided with protective members 10 respectively formed of a rubber or the like for protecting those branching portions.

Figure 6:
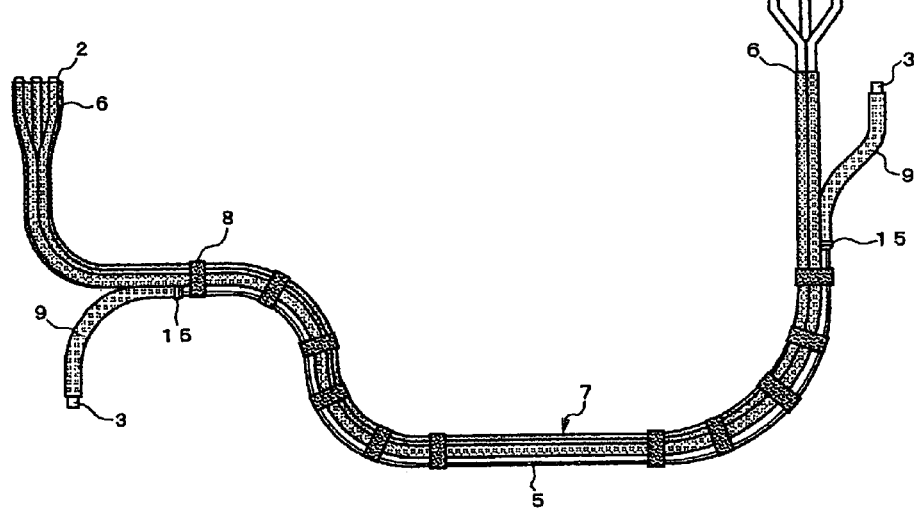
FIG. 6 is a plan view showing providing a shielded wire to ends of the metallic pipe in the method for producing the vehicle electrical conduction path shown in FIGS. 1A and 1B.

Also, the ends of the metallic pipe 5 are electrically connected with one end of flexible shielded wires 9 respectively, so that a periphery of the control cable 3 extended out from the end of the metallic pipe 5 is covered with those shielded wires 9 respectively (see FIG. 6). The shielded wires 9 are formed of a braided shield, for example, and the other end thereof is electrically connected with a shield case for a device not shown to which the control cable 3 is connected. That is, the shielded wires 9 serve both to electrically connect the metallic pipe 5 to the shield case of the device, and to shield the control cable 3 extended out from the metallic pipe 5.

The ends of the control cable 3 and the shielded wires 9 extended out from the protective members 10 to the device sides are fitted into terminal corrugated tubes 11 respectively. The ends of the control cable 3 are provided with connecting terminals 16 to be connected to the devices (not shown) respectively.

On the other hand, the braided shield 6 extended out from the ends of the corrugated tube 4 is configured to be electrically connected with the shield case for the device (not shown) to which the plural power cables 2 are connected. The ends of the power cable bundle 7 extended out from the protective members 10 to the device sides are fitted into terminal corrugated tubes 12 respectively. The ends of the power cables 2 are provided with a connector 13 or a connecting terminal 14 for being connected to the devices. In FIG. 1A, a portion of the connector 13 is indicated by the broken-out section.

A method for producing the vehicle electrical conduction path 1 is described next.

Figure 2A:
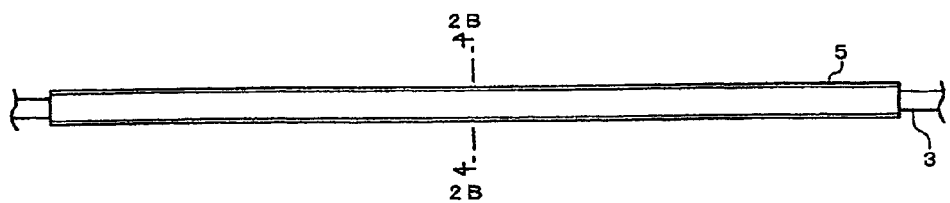
FIG. 2A is a plan view showing accommodating a control cable in a metallic pipe in a method for producing the vehicle electrical conduction path shown in FIGS. 1A and 1B.
Figure 2B:
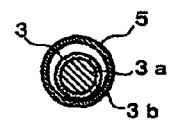
FIG. 2B is a cross-sectional view taken along line 2B-2B in FIG. 2A.
Figure 3:
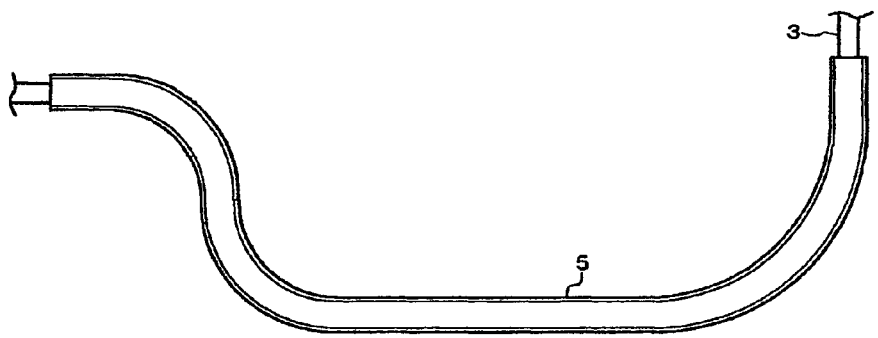
FIG. 3 is a plan view showing forming the metallic pipe into a desired shape in a method for producing the vehicle electrical conduction path shown in FIGS. 1A and 1B.

When producing the vehicle electrical conduction path 1, the control cable 3 is first passed into the metallic pipe 5 as shown in FIGS. 2A and 2B. Referring to FIG. 3, the metallic pipe 5 with the control cable 3 passed therein is then formed by mechanical bending (a bender) into a desired shape.

Figure 4A:
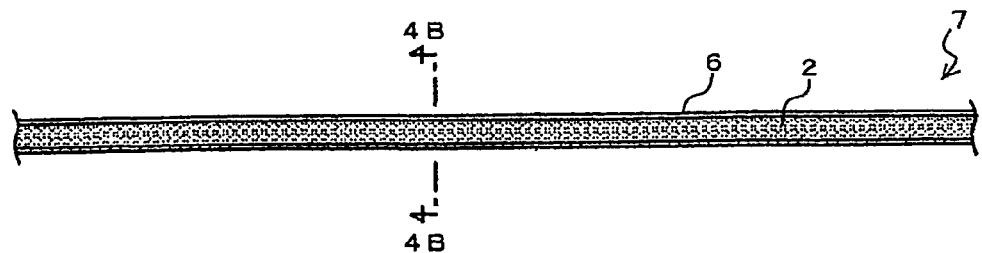
FIG. 4A is a plan view showing a power cable bundle in the method for producing the vehicle electrical conduction path shown in FIGS. 1A and 1B.
Figure 4B:
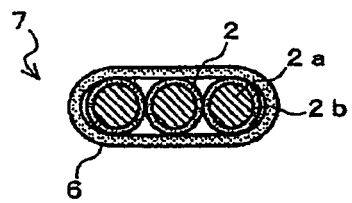
FIG. 4B is a cross-sectional view taken along line 4B-4B in FIG. 4A.
Figure 5A:
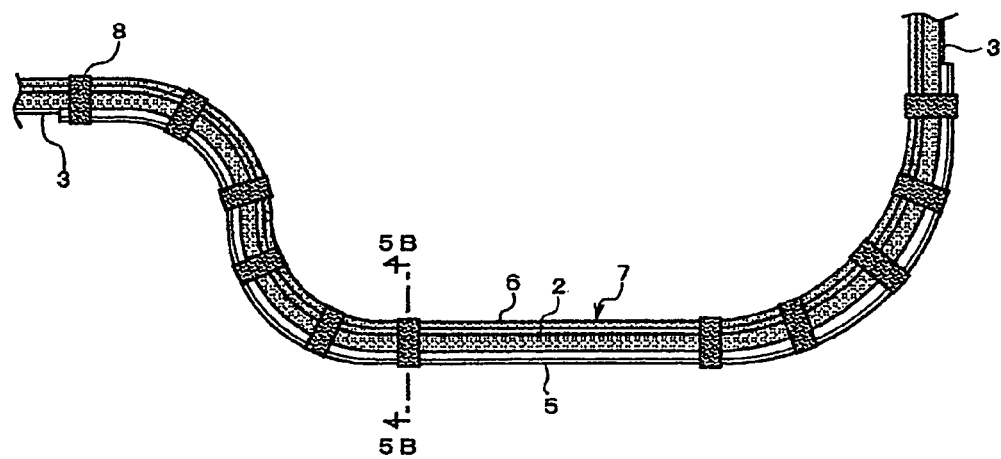
FIG. 5A is a plan view showing fixing the power cable bundle along and to the formed metallic pipe with a taping material in the method for producing the vehicle electrical conduction path shown in FIGS. 1A and 1B.
Figure 5B:
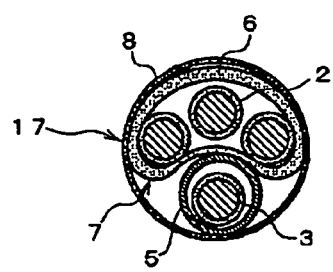
FIG. 5B is a cross-sectional view taken along line 5B-5B in FIG. 5A.

Referring to FIGS. 4A and 4B, the plural power cables 2 are thereafter bundled with the braided shield 6 to form the power cable bundle 7. Referring to FIGS. 5A and 5B, the power cable bundle 7 is arranged along the formed metallic pipe 5, and the metallic pipe 5 and the power cable bundle 7 are bound and fixed together at positions longitudinally spaced a predetermined pitch apart using the taping material 8.

After fixing the metallic pipe 5 and the power cable bundle 7, referring to FIG. 6, the ends of the metallic pipe 5 are electrically connected with the shielded wires 9 respectively, so that the periphery of the control cable 3 extended out from the end of the metallic pipe 5 is covered with those shielded wires 9 respectively. The shielded wires 9 are attached by use of metal bands 15 to the ends, respectively, of the metallic pipe 5.

Figure 7:
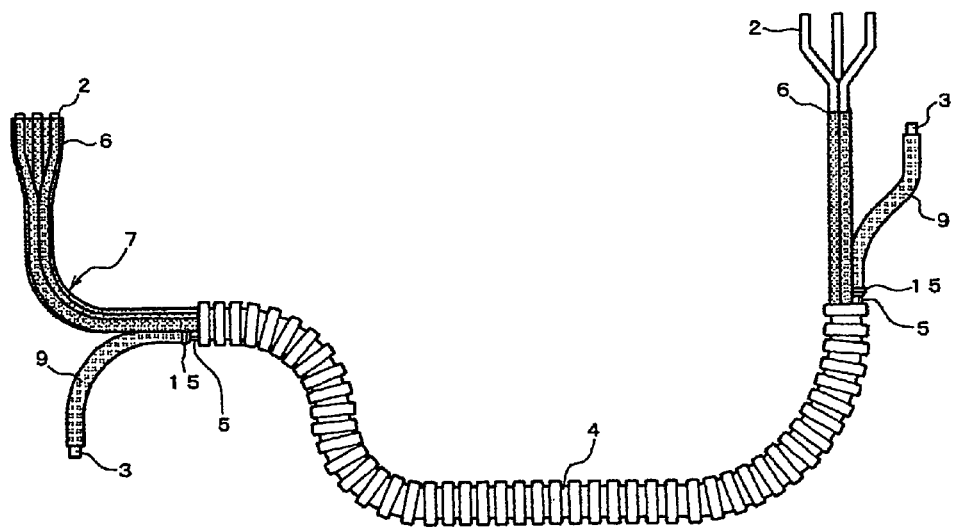
FIG. 7 is a plan view showing covering the metallic pipe and the power cable bundle with a corrugated tube in the method for producing the vehicle electrical conduction path 1 shown in FIGS. 1A and 1B.

After attaching the shielded wires 9 to the metallic pipe 5, referring to FIG. 7, the metallic pipe 5 with the control cable 3 accommodated therein, and the power cable bundle 7 are covered with the corrugated tube 4. Referring to FIG. 8, the portions from which the control cable 3 and the power cable bundle 7 branch are provided with the protective members 10 respectively. The protective members 10 are provided to leave no gap between them and the corrugated tube 4.

Thereafter, the ends of the control cable 3 and the shielded wires 9 extended out from the protective members 10 to the device sides are fitted into the terminal corrugated tubes 11 respectively, while the ends of the power cable bundle 7 extended out from the protective members 10 to the device sides are fitted into the terminal corrugated tubes 12 respectively. The ends of the control cable 3 are provided with the connecting terminals 16 respectively, while the ends of the power cables 2 are provided with the connector 13 or the connecting terminal 14. This results in the vehicle electrical conduction path 1 as shown in FIGS. 1A and 1B.

(Operation and Advantages of the First Embodiment)

Operation and advantages of the embodiment are described.

In the vehicle electrical conduction path 1 in this embodiment, the control cable 3 is accommodated in the metallic pipe 5, and the metallic pipe 5 with the control cable 3 accommodated therein is formed or molded into a desired shape, thereby holding the control cable 3 in the desired shape, and the power cable bundle 7 comprising the plural power cables 2 bundled with the braided shield 6 is arranged along the formed metallic pipe 5, and a periphery thereof is covered with the corrugated tube 4.

Since the metallic pipe 5 with the control cable 3 accommodated therein is formed into the desired shape, the entire vehicle electrical conduction path 1 can be held in the desired wiring shape (layout). In addition, the metallic pipe 5 with the control cable 3 accommodated therein and the power cable bundle 7 may be accommodated in the pre-colored corrugated tube 4, to thereby allow omission of the conventional painting step. This allows realization of the vehicle electrical conduction path 1 which is easy in production, and which can consequently be reduced in cost. Also, in this embodiment, since the metallic pipe 5 is not painted, recycling is easy in comparison with the prior art where the metallic pipe 5 is painted.

Further, in the vehicle electrical conduction path 1, since the plural power cables 2 are collectively bundled with the braided shield 6, noise (electromagnetic waves) caused in the power cables 2 can be inhibited from radiating by the braided shield 6, and since the control cable 3 is accommodated in the metallic pipe 5, the control cable 3 is consequently doubly shielded, thereby allowing the noise caused in the power cables 2 to be further inhibited from affecting electrical signals propagating in the control cable 3. This allows the use of the power cables 2 and the control cable 3 which have no shielding external conductor and which are therefore inexpensive, leading to cost reduction.

Also, in the vehicle electrical conduction path 1, since only the plural power cables 2 are collectively bundled with the braided shield 6, and the plural power cables 2 bundled with the braided shield 6 are arranged along the metallic pipe 5 with the control cable 3 accommodated therein, the power cables 2 and the control cable 3 are easily allowed to branch. Further, although IP-A-2007-87628, for example, needs to provide the power cable branching from the control cable with the separate shield for inhibiting noise from radiating out, the branching portions of the power cables 2 of the vehicle electrical conduction path 1 are being covered with the braided shield 6 and therefore do not have to be provided with a separate shield. This allows the ease of connection of the power cables 2 to the devices.

Also, in the vehicle electrical conduction path 1, the control cable 3 extended out from the metallic pipe 5 is allowed to be connected directly to the devices. This allows the ease of connection of the control cable 3 to the devices. Although in this embodiment it has been described that the ends of the metallic pipe 5 are provided with the shielded wires 9 respectively, the shielded wires 9 may be omitted by extending the metallic pipe 5 to near the devices to connect, and shortening the exposed distance of the control cable 3. When the shielded wires 9 are omitted, the metallic pipe 5 may be connected to ground using a separately prepared electric cable.

Further, since the vehicle electrical conduction path 1 is configured so that the power cables 2 bundled with the braided shield 6 are arranged (in a substantially C-shape) along the metallic pipe 5 with the control cable 3 accommodated therein, it is possible to save the size of the vehicle electrical conduction path 1 in comparison with the configuration of JP-A-2007-87628, for example, in which the power cables 2 are further covered with a metallic pipe therearound.

The metallic pipe 5 and the power cables 2 are also considered as being configured to be bundled with the braided shield 6. In this case, however, the power cables 2 and the control cable 3 are difficult to branch as described above. Further, since the power cables 2 and the metallic pipe 5 relatively freely move relative to each other, a fault such as wear or a break in the power cables 2 may be caused by the power cables 2 and the metallic pipe 5 contacting each other due to vibration. In the vehicle electrical conduction path 1, since the plural power cables 2 are bundled with the braided shield 6, and firmly fixed to the metallic pipe 5 with the taping material 8, no fault such as wear or break due to vibration is not likely to occur.

Also, in the vehicle electrical conduction path 1, the metallic pipe 5 may be made small in diameter, so that the metallic pipe 5 is unlikely to buckle even when bent at a small bending radius, in comparison with the conventional vehicle electrical conduction path being entirely surrounded by the thick metallic pipe. Thus, the thickness of the metallic pipe 5 is allowed to be thinned, so as to lessen wasteful use of the material for the metallic pipe 5.

Also, the vehicle electrical conduction path 1 is allowed to be reduced in weight because of being configured to be not entirely surrounded by the metallic pipe 5. Tables 1 to 3 show results of one example of comparing weights per unit length of the conventional vehicle electrical conduction path (prior art) having three power cables and one (shielded) control cable surrounded by the metallic pipe, and the present vehicle electrical conduction path 1 (present invention).

TABLE 1

| Prior art | | Present invention | |
|---|---|---|---|
| Member name | Weight per unit length (g/m) | Member name | Weight per unit length (g/m) |
| Aluminum pipe (inside diameter 23.0 mm, thickness 1.2 mm) | 245 | Aluminum pipe (inside diameter 9.0 mm, thickness 1.2 mm) | 105 |
| Control cable with shield and sheath | 240 | Control cable with no shield | 130 |
| 3 power cables | 450 | 3 power cables | 450 |
| | | Braided shield (copper wire diameter 0.18 mm) | 135 |
| | | Corrugated tube (inside diameter 25.0 mm) | 45 |
| Total | 935 | Total | 865 |

TABLE 2

| Prior art | | Present invention | |
|---|---|---|---|
| Member name | Weight per unit length (g/m) | Member name | Weight per unit length (g/m) |
| Aluminum pipe (inside diameter 23.0 mm, thickness 1.2 mm) | 245 | Aluminum pipe (inside diameter 9.0 mm, thickness 1.5 mm) | 135 |
| Control cable with shield and sheath | 240 | Control cable with no shield and sheath | 130 |
| 3 power cables | 450 | 3 power cables | 450 |
| | | Braided shield (copper wire diameter 0.18 mm) | 135 |
| | | Corrugated tube (inside diameter 25.0 mm) | 45 |
| Total | 935 | Total | 895 |

TABLE 3

| Prior art | | Present invention | |
|---|---|---|---|
| Member name | Weight per unit length (g/m) | Member name | Weight per unit length (g/m) |
| Aluminum pipe (inside diameter 23.0 mm, thickness 1.2 mm) | 245 | Aluminum pipe (inside diameter 9.0 mm, thickness 1.8 mm) | 165 |
| Control cable with shield and sheath | 240 | Control cable with no shield and sheath | 130 |
| 3 power cables | 450 | 3 power cables | 450 |
| | | Braided shield (copper wire diameter 0.18 mm) | 135 |
| | | Corrugated tube (inside diameter 25.0 mm) | 45 |
| Total | 935 | Total | 925 |

Table 1 shows the case using a 9.0 mm inside diameter and 1.2 mm thick aluminum pipe as the metallic pipe 5, Table 2 shows the case using a 9.0 mm inside diameter and 1.5 mm thick aluminum pipe as the metallic pipe 5, and Table 3 shows the case using a 9.0 mm inside diameter and 1.8 mm thick aluminum pipe as the metallic pipe 5.

As shown in Tables 1 to 3, whereas the weight per unit length (1 m) of the conventional vehicle electrical conduction path (prior art) is 935 g, the weight per unit length of the vehicle electrical conduction path 1 in the example of the present invention can be reduced to from 865 to 925 g. From the point of view of weight reduction, it is desirable that the metallic pipe 5 be thinned, but because when too thin, the metallic pipe 5 is likely to sag under its own weight due to its mechanical strength decreasing, and needs strength for supporting its own weight when the vehicle electrical conduction path 1 is long, the thickness of the metallic pipe 5 should be selected taking account of the length of the vehicle electrical conduction path 1. For example, the thickness of the metallic pipe 5 considered to be selected is configured as follows: When the length of the vehicle electrical conduction path 1 (i.e. the length of the metallic pipe 5) to be fixed in shape is as short as less than 1.5 m, the thickness of the metallic pipe 5 is 1.2 mm or less; when the length of the vehicle electrical conduction path 1 to be fixed in shape is from 1.5 to 2.5 m, the thickness of the metallic pipe 5 is 1.5 mm; and when the length of the vehicle electrical conduction path 1 to be fixed in shape exceeds 2.5 in, the thickness of the metallic pipe 5 is 1.8 mm or more. In Tables 1 to 3, the weight of the braided shield 6 has been estimated as being 135 g/m by assuming the use of a 0.18 mm outside diameter copper wire, but the weight of the braided shield 6 is likely to be further reduced by reducing the wire size (e.g. to 0.12 mm), or by using an aluminum wire.

Second Embodiment

A second preferred embodiment according to the invention is described next.

(Vehicle Electrical Conduction Path 91)

Referring to FIG. 9, a vehicle electrical conduction path 91 is basically configured as with the vehicle electrical conduction path 1 shown in FIGS. 1A and 1B, but the arrangement and shape of the power cables 2 (the shape of the power cable bundle 7) are different therefrom.

Although the vehicle electrical conduction path 1 shown in FIGS. 1A and 1B has the three power cables 2 arranged in a substantially C-shape in its cross-sectional view along a periphery of the metallic pipe 5, the vehicle electrical conduction path 91 of FIG. 9 has the power cable bundle 7 formed of the three power cables 2 bundled in a substantially triangular shape in its cross-sectional view, and arranged along one side of the metallic pipe 5. When the horizontal direction in FIG. 9 is the width direction of the vehicle electrical conduction path 91, and the vertical direction in FIG. 9 is the height direction of the vehicle electrical conduction path 91, the vehicle electrical conduction path 91 has the power cable bundle 7 arranged along a side surface in the width direction of the metallic pipe 5.

Either one length in the height or width direction of the vehicle electrical conduction path 91 may be made smaller for a constraint on installation space therefor. The vehicle electrical conduction path 91 of FIG. 9 allows its height to be smaller than its width, so that its height may be smaller in comparison with the vehicle electrical conduction path 1 having the circular cross section as shown in FIG. 1B. For example, whereas the maximum height of the vehicle electrical conduction path 1 of FIG. 1B is 30 mm, the maximum height of the vehicle electrical conduction path 91 of FIG. 9 can be made as small as approximately 25 mm. This is described in detail below.

In the vehicle electrical conduction path 1 shown in FIG. 1B, the outside diameter of the harness 17 comprising the power cable bundle 7 and the metallic pipe 5 bound with the taping material 8 is 22.0 mm as a total of sizes of the respective parts, the metallic pipe 5 and the taping material 8. Since the harness 17 is accommodated in the 25.0 mm inside diameter and 30.0 mm maximum outside diameter corrugated tube 4 as described above, the maximum outside diameter (maximum height) of the vehicle electrical conduction path 1 itself is also 30.0 mm. The corrugated tube 4 has the inside diameter clearance of approximately 3.0 mm relative to the outside diameter of the harness 17 being 22.0 mm. This is because when the harness 17 held in the desired shape is accommodated into the corrugated tube 4, without this degree of clearance, it is not likely to be easily accommodated thereinto, and what is worse, it is not likely to be able to be accommodated thereinto.

In the vehicle electrical conduction path 91 of FIG. 9, the vertical height in FIG. 9 of the power cable bundle 7 is 16.0 mm. The vertical height in FIG. 9 of the harness 17 comprising the power cable bundle 7 and the metallic pipe 5 bound with the 0.5 mm thick taping material 8 is 17.0 mm. When this harness 17 is accommodated in the corrugated tube 94 having the inside diameter clearance of approximately 3.0 mm for the above-explained reason, the maximum height of the vehicle electrical conduction path 91 is approximately 25 mm. The corrugated tube 4, the corrugated tube 94, and a later-described corrugated tube 104 are all 5.0 mm in the difference between the inside diameter and the maximum outside diameter thereof.

To allow the vehicle electrical conduction path 91 to have its width to be smaller than its height, the power cable bundle 7 may be arranged along a side surface in the height direction of the metallic pipe 5.

(Modification to the Second Embodiment)
(Vehicle Electrical Conduction Path 101)

Figure 10:
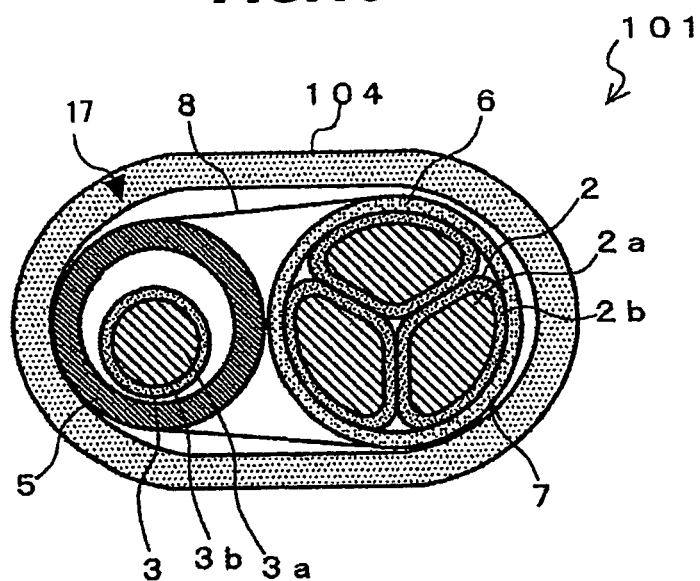
FIG. 10 is a cross-sectional view showing a vehicle electrical conduction path in a modification to the second embodiment according to the invention.

A vehicle electrical conduction path 101 in a modification to the second embodiment shown in FIG. 10 comprises the vehicle electrical conduction path 91 of FIG. 9 whose power cable bundle 7 is formed by forming each of the power cables 2 in a fan shape in cross section, stranding the fan cross section shape power cables 2 together, and providing the stranded power cables 2 with the braided shield 6 therearound.

This vehicle electrical conduction path 101 allows the outside diameter of the power cable bundle 7 to be even smaller in comparison with the vehicle electrical conduction path 91 of FIG. 9. It is therefore possible to realize the smaller size vehicle electrical conduction path 101. When using the fan cross section shape power cables 2, the vertical height in FIG. 10 of the power cable bundle 7 is 14.5 mm, and the vertical height in FIG. 10 of the harness 17 is 15.5 mm. When this harness 17 is accommodated in the corrugated tube 104 having the inside diameter clearance of approximately 3.0 mm and the difference between the inside diameter and the maximum outside diameter of 5.0 mm, the maximum height of the vehicle electrical conduction path 101 is approximately 23.5 mm.

In this manner, the vehicle electrical conduction paths 91 and 101 can adapt to various layouts according to the vehicle type.

The invention is not limited to the above embodiments, but it is apparent that various alterations may be made without departing from the spirit and scope of the invention.

Although in the above embodiments it has been described, for example, that one control cable 3 is accommodated in the metallic pipe 5, two or more control cables 3 may be accommodated in the metallic pipe 5, or a cable other than the control cable 3, such as an auxiliary power cable, may be accommodated in the metallic pipe 5.

Third Embodiment

A third preferred embodiment according to the invention is described next.

(Vehicle Electrical Conduction Path 111)

Figure 11:
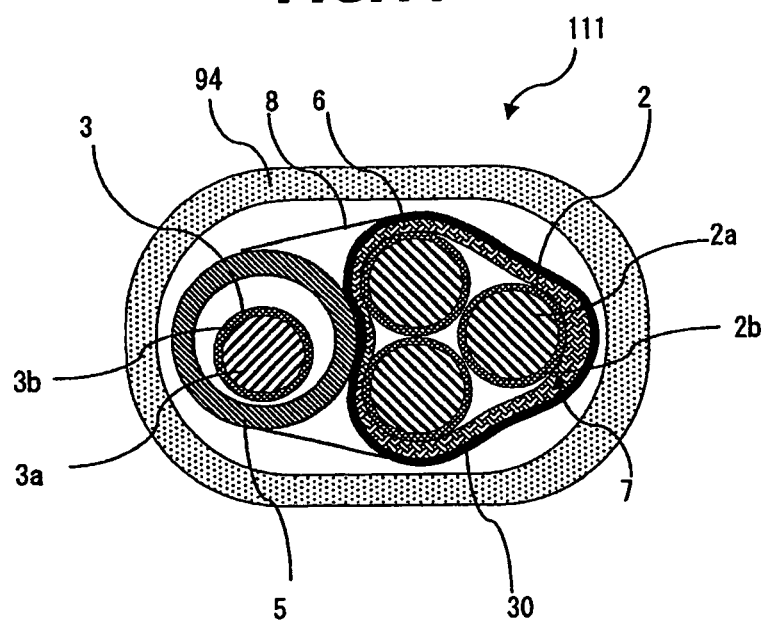
FIG. 11 is a cross-sectional view showing a vehicle electrical conduction path in a third embodiment according to the invention.

FIG. 11 is a cross-sectional view showing a vehicle electrical conduction path 111 in the third embodiment according to the invention.

The vehicle electrical conduction path 111 shown in FIG. 11 is basically configured as with the vehicle electrical conduction path 91 of FIG. 9, but differs therefrom in that an insulating layer 30 is provided between the metallic pipe 5 and the braided shield 6.

The insulating layer 30 in FIG. 11 is a sheath formed around the braided shield 6. In this embodiment, the insulating layer 30 is formed of a resin tube, and the power cable bundle 7 is inserted into this resin tube 30. This results in the insulating layer 30 formed around the braided shield 6. The insulating layer 30 is from 0.03 to 0.1 mm in thickness. The insulating layer 30 is preferred to be heat resistant and fire retardant, and may use a resin such as a polyolefin or a polyvinyl chloride.

The vehicle electrical conduction path 111 allows the metallic pipe 5 and the braided shield 6 to be prevented from contacting each other by the insulating layer 30 provided therebetween. It is therefore possible to enhance the reliability of the vehicle electrical conduction path 111. This is described in detail below.

If the metallic pipe 5 and the braided shield 6 are in contact with each other, the braided shield 6 is likely to wear in the contact area due to vehicle vibration. In this case, the braided shield 6 deteriorates in its shielding function, and a sensor and the like mounted on the vehicle are therefore adversely affected by noise resulting from the power cables 2. However, because the vehicle electrical conduction path 111 in this embodiment is provided with the insulating layer 30 between the metallic pipe 5 and the braided shield 6, the metallic pipe 5 and the braided shield 6 are prevented from contacting each other, so that the wear of the braided shield 6 due to vehicle vibration may be reduced. This allows the braided shield 6 to be inhibited from deteriorating in its shielding function. It is therefore possible to enhance the reliability of the vehicle electrical conduction path 111.

Also, if the vehicle electrical conduction path 111 is provided to be exposed in a lower portion of the vehicle body, a portion of the corrugated tube 94 is likely to be broken by flying stone striking, and water is likely to penetrate the broken portion into the vehicle electrical conduction path 111, and contact the metallic pipe 5 or the braided shield 6. In this case, when the metallic pipe 5 and the braided shield 6 are formed of differing metals, and are in contact with each other, conspicuous bimetallic corrosion (Galvanic corrosion) is likely to be caused in the contact portion by the contact of the differing metals, leading to corrosion of the braided shield 6. However, because the vehicle electrical conduction path 111 in this embodiment is provided with the insulating layer 30 between the metallic pipe 5 and the braided shield 6, the metallic pipe 5 and the braided shield 6 are prevented from contacting each other, thereby allowing prevention of the Galvanic corrosion between the metallic pipe 5 and the braided shield 6. This permits prevention of the corrosion of the braided shield 6. It is therefore possible to enhance the reliability of the vehicle electrical conduction path 111.

Also, in this embodiment, the insulating layer 30 with which the periphery of the braided shield 6 is covered advantageously serves to protect the braided shield 6 from flying stone striking.

Although in this embodiment the insulating layer 30 is for covering the periphery of the braided shield 6, it may be for covering the periphery of the metallic pipe 5. When the outside diameter of the metallic pipe 5 is smaller than the outside diameter of the power cable bundle 7, the periphery of the metallic pipe 5 is covered with the insulating layer 30, thereby allowing avoidance of an increase in the height of the corrugated tube 94.

Although the above vehicle electrical conduction path 111 has been formed with the insulating layer 30 around the braided shield 6 by inserting the power cable bundle 7 into the resin tube 30, the insulating layer 30 around the braided shield 6 may be formed by wrapping an insulating tape around the power cable bundle 7. The insulating tape used is preferred to be heat resistant and fire retardant, and may be formed of a heat resistant polyvinyl chloride, for example. There are the following ways to wrap the insulating tape: The insulating tape may be wrapped in a cross sectional circumferential direction of the power cable bundle 7, or lapped lengthwise in a longitudinal direction of the power cable bundle 7. Further, the insulating tape is preferred to have an adhesive layer on one side, to be able to ensure the close adhesion of the overlapping surface of the insulating tape.

Also, when there are contact and non-contact portions of between the metallic pipe 5 and the braided shield 6, the insulating layer 30 may be formed only in the contact portion thereof with the above-described method.

(Modifications to the Third Embodiment)
(Vehicle Electrical Conduction Path 121)

A vehicle electrical conduction path 121 in a modification to the third preferred embodiment according to the invention is described next.

Figure 12:
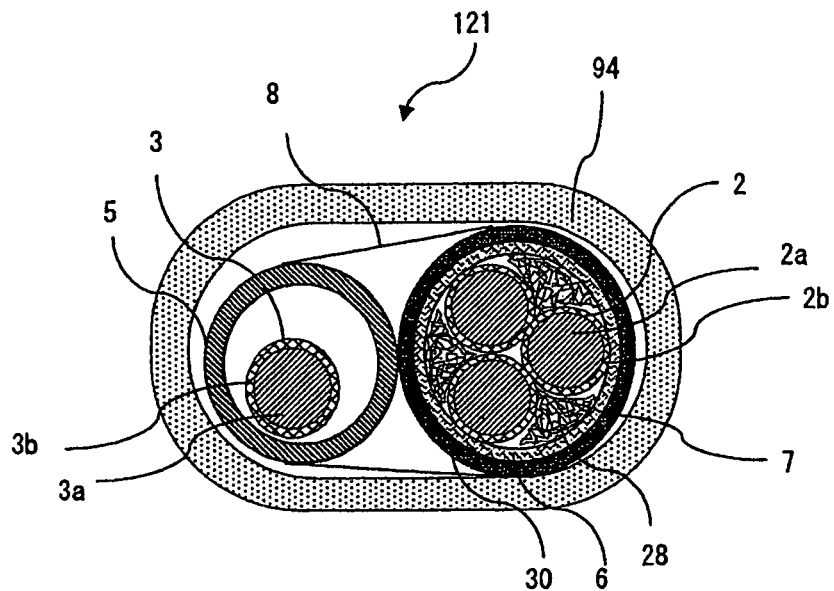
FIG. 12 is a cross-sectional view showing a vehicle electrical conduction path in a modification to the third embodiment according to the invention.

FIG. 12 is a cross-sectional view showing the vehicle electrical conduction path 121 in the modification to the third embodiment according to the invention.

The vehicle electrical conduction path 121 shown in FIG. 12 is basically configured as with the vehicle electrical conduction path 111 of FIG. 11, but differs therefrom in that the insulating layer (sheath) 30 is extruded and formed to cover the braided shield 6. In this case, in order for the insulating layer 30 to uniformly cover the braided shield 6, it is preferable that a filler 28 be interposed between the power cables 2, and that the power cable bundle 7 be formed in a substantially circular shape in its cross-sectional view. The filler 28 may use a polypropylene string, for example.

(Vehicle Electrical Conduction Path 131)

A vehicle electrical conduction path 131 in a modification to the third preferred embodiment according to the invention is described next.

Figure 13:
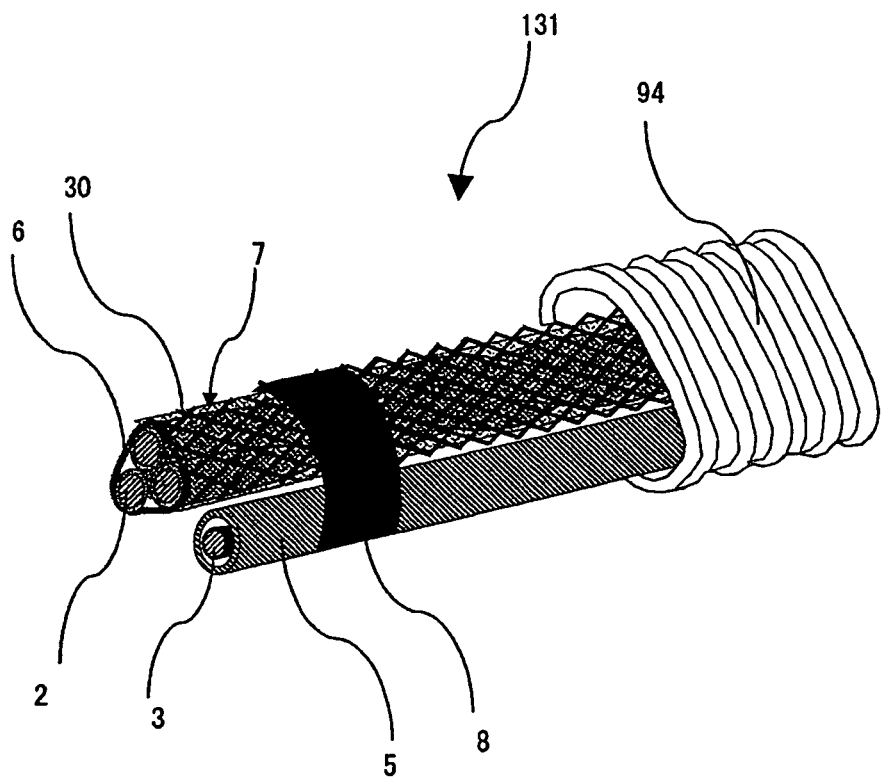
FIG. 13 is a cross-sectional view showing a vehicle electrical conduction path in a modification to the third embodiment according to the invention.

FIG. 13 is a cross-sectional view showing the vehicle electrical conduction path 131 in the modification to the third embodiment according to the invention.

The vehicle electrical conduction path 131 shown in FIG. 13 is basically configured as with the vehicle electrical conduction path 111 of FIG. 11, but differs therefrom in that the insulating layer 30 is formed in a mesh-like shape.

The insulating layer 30 in FIG. 13 is formed of a mesh-like resin tube, and the power cable bundle 7 is inserted into this mesh-like resin tube 30. This results in the insulating layer 30 formed around the braided shield 6. In this modification to the third embodiment, the insulating layer 30 made of the mesh-like resin tube provided between the metallic pipe 5 and the braided shield 6 allows avoidance of direct contact of the metallic pipe 5 and the braided shield 6. The mesh-like resin tube 30 material may use a polyolefin-based resin, for example. Also, although in this modification to the third embodiment the insulating layer 30 has been formed around the braided shield 6 by inserting the power cable bundle 7 into the mesh-like resin tube 30, the mesh-like insulating layer 30 around the braided shield 6 may be formed by forming, for example, a polyolefin-based resin into a stringy shape, and winding it crosswise around the power cable bundle 7.

The vehicle electrical conduction path 131 provided with the mesh-like insulating layer 30 between the metallic pipe 5 and the braided shield 6 can have the same advantageous effect as the vehicle electrical conduction path 111 in the third embodiment, and allows reduction of the amount of the insulating layer 30 material because the insulating layer 30 is formed in the mesh-like shape. Therefore, the vehicle electrical conduction path 131 allows contribution to reduction of material cost and weight of the insulating layer 30. The mesh-like resin tube insulating layer 30 may be provided around the metallic pipe 5.

Although the invention has been described, the invention according to claims is not to be limited by the above-mentioned embodiments and examples. Further, please note that not all combinations of the features described in the embodiments and the examples are not necessary to solve the problem of the invention.

What is claimed is:

1. A vehicle electrical conduction path, comprising:
plural power cables;
a braided shield which bundles and shields the plural power cables;
a control cable;
a metallic pipe which accommodates the control cable separately from the plural power cables; and
a flexible resin tube which covers a periphery of the metallic pipe and the plural power cables bundled with the braided shield and arranged along the metallic pipe, the flexible resin tube being pre-colored with a predetermined color for indicating a high voltage portion,
wherein the metallic pipe is configured to hold the control cable in a desired shape.

2. The vehicle electrical conduction path according to claim 1, wherein the metallic pipe accommodates only the control cable.

3. The vehicle electrical conduction path according to claim 1, wherein the metallic pipe is formable in a desired shape for accommodating the control cable.

4. The vehicle electrical conduction path according to claim 1, wherein a rigidity of the metallic pipe is greater than a rigidity of the flexible resin tube.

5. The vehicle electrical conduction path according to claim 1, wherein the control cable is accommodated in the metallic pipe and the metallic pipe accommodating the control cable is formed in a desired shape, thereby holding the control cable in the desired shape of the metallic pipe.

6. The vehicle electrical conduction path according to claim 1, wherein an end of the metallic pipe is electrically connected with one end of a flexible shielded wire, a periphery of the control cable extended out from the end of the metallic pipe is covered with the shielded wire, and another end of the shielded wire extended out from an end of the resin tube is configured to be electrically connected with a shield case for a device to which the control cable is connected.

7. The vehicle electrical conduction path according to claim 1, wherein the braided shield extended out from an end of the resin tube is configured to be electrically connected with a shield case for a device to which the plural power cables are connected.

8. The vehicle electrical conduction path according to claim 1, further comprising:
   a protective member for protecting a branching portion at an end of the resin tube, from which the plural power cables bundled with the braided shield and the control cable branch.

9. The vehicle electrical conduction path according to claim 8, wherein portions of the control cable and the plural power cables bundled with the braided shield are extended from the branching portion and fitted into flexible resin terminal tubes, respectively.

10. The vehicle electrical conduction path according to claim 1, wherein the resin tube comprises a corrugated tube.

11. The vehicle electrical conduction path according to claim 1, wherein the metallic pipe is formed into a desired shape, prior to the plural power cables bundled with the braided shield being arranged along the metallic pipe.

12. The vehicle electrical conduction path according to claim 1, wherein the metallic pipe and the plural power cables bundled with the braided shield are made integral with each other by being bound with a taping material.

13. The vehicle electrical conduction path according to claim 1, wherein the plural power cables bundled with the braided shield are arranged in a substantially C-shape in its cross-sectional view along a periphery of the metallic pipe, and a periphery of the plural power cables with the braided shield and the metallic pipe is covered with the resin tube having a circular cross section.

14. The vehicle electrical conduction path according to claim 1, wherein the plural power cables bundled with the braided shield are arranged along one side of the metallic pipe, and a periphery of the plural power cables with the braided shield and the metallic pipe is covered with the resin tube having an elliptic cross section.

15. The vehicle electrical conduction path according to claim 1, further comprising:
   an insulating layer provided between the metallic pipe and the braided shield.

16. The vehicle electrical conduction path according to claim 15, wherein the insulating layer covers at least one of a periphery of the metallic pipe and a periphery of the braided shield.

17. The vehicle electrical conduction path according to claim 15, wherein the insulating layer is formed in a mesh-like shape.

18. The vehicle electrical conduction path according to claim 1, wherein the metallic pipe consists essentially of aluminum, and a thickness of the metallic pipe is not less than 1 mm.

19. The vehicle electrical conduction path according to claim 1, wherein the plural power cables are bundled with the braided shield at a branching portion of the plural power cables at an end of the resin tube.

20. The vehicle electrical conduction path according to claim 1, wherein the control cable and a power cable bundle branch out at ends of the resin tube.

* * * * *